US009848793B2

(12) United States Patent
Yoo et al.

(10) Patent No.: US 9,848,793 B2
(45) Date of Patent: Dec. 26, 2017

(54) MACHINE-BASED PATIENT-SPECIFIC SEIZURE CLASSIFICATION SYSTEM

(71) Applicant: Masdar Institute of Science and Technology, Abu Dhabi (AE)

(72) Inventors: Jerald Yoo, Abu Dhabi (AE); Muhammad Awais Bin Altaf, Abu Dhabi (AE)

(73) Assignee: Masdar Institute of Science and Technology (AE)

( * ) Notice: Subject to any disclaimer, the term of this patent is extended or adjusted under 35 U.S.C. 154(b) by 645 days.

(21) Appl. No.: 14/182,570

(22) Filed: Feb. 18, 2014

(65) Prior Publication Data

US 2014/0235990 A1    Aug. 21, 2014

Related U.S. Application Data

(60) Provisional application No. 61/765,280, filed on Feb. 15, 2013.

(51) Int. Cl.
*A61B 5/04* (2006.01)
*A61B 5/00* (2006.01)
*A61B 5/0478* (2006.01)

(52) U.S. Cl.
CPC ........ *A61B 5/04017* (2013.01); *A61B 5/4094* (2013.01); *A61B 5/0478* (2013.01);
(Continued)

(58) Field of Classification Search
None
See application file for complete search history.

(56) References Cited

U.S. PATENT DOCUMENTS

| 6,792,304 B1* | 9/2004 | Silberstein | ......... A61B 5/04842 600/300 |
| 2001/0047127 A1* | 11/2001 | New, Jr. | ............... A61B 5/0002 600/300 |

(Continued)

FOREIGN PATENT DOCUMENTS

WO    2013123358 A1    8/2013

OTHER PUBLICATIONS

Amari et al. Improving support vector machine classifiers by modifying kernel functions. Neural Networks 12 (1999) 783-789.*

(Continued)

*Primary Examiner* — Etsub Berhanu
(74) *Attorney, Agent, or Firm* — Grossman Tucker Perreault & Pfleger PLLC

(57) ABSTRACT

This disclosure is directed to a machine-based patient-specific seizure classification system. In general, an example system may comprise a non-linear SVM seizure classification system-on-chip (SoC) with multichannel EEG data acquisition and storage for epileptic patients is presented. The SoC may integrate a hardware-efficient log-linear Gaussian Basis Function engine, floating point piecewise linear natural log, and low-noise, high dynamic range readout circuits. In at least one example implementation, the SoC may consume 1.83 µJ/classification while classifying 8 channel results with an average detection rate, average false alarm rate and latency of 95.1%, 0.94% and <2 s, respectively.

19 Claims, 12 Drawing Sheets

(52) U.S. Cl.
CPC ............. *A61B 5/4836* (2013.01); *A61B 5/725* (2013.01); *A61B 2503/04* (2013.01); *A61B 2503/06* (2013.01)

(56) References Cited

U.S. PATENT DOCUMENTS

| | | | |
|---|---|---|---|
| 2005/0215916 A1* | 9/2005 | Fadem | A61B 5/04004 600/544 |
| 2008/0188721 A1* | 8/2008 | Patangay | A61B 5/0031 600/301 |
| 2010/0280334 A1* | 11/2010 | Carlson | A61N 1/36082 600/301 |
| 2011/0077697 A1* | 3/2011 | Rofougaran | G06F 19/323 607/2 |
| 2012/0296175 A1* | 11/2012 | Poh | A61B 5/02405 600/301 |
| 2013/0080808 A1 | 3/2013 | Verma et al. | |

OTHER PUBLICATIONS

Tsuji et al. A Log-Linearized Gaussian Mixture Network and Its Application to EEG Pattern Classification. IEEE Transactions on Systems, Man, and Cybernetics—Part C: Applications and Reviews, vol. 29, No. 1, Feb. 1999.*

Yoo, Jerald et al, "An 8-Channel Scalable EEG Acquisition SoC With Fully Integrated Patient-Specific Seizure Classification and Recording Processor", ISSCC 2012/Session 17/ Diagnostic & Therapeutic Technologies for Health/17.1, Feb. 21, 2012, pp. 292-294.

Bin Altaf, Muhammad Awais et al, "A 1.83μJ/Classification Non-linear Support-Vector-Machine-Based Patient-Specific Seizure Classification SoC", ISSCC 2013/Session 6/ Emerging Medical and Sensor Technologies/6.2, Feb. 18, 2013, pp. 100-102.

Yoo, Jerald et al, "An 8-Channel Scalable EEG Acquisition SoC With Patient-Specific Seizure Classification and Recording Processor", IEEE Journal of Solid-State Circuits, vol. 48, No. 1, Jan. 2013, pp. 214-228.

* cited by examiner

500

| Process | 0.18um 1P6M CMOS |
|---|---|
| Area | 5.0 x 5.0 mm |
| Supply Voltage | 1.8V (AFE) 1.0V (DBE) |
| Channel | 1 to 8 Scalable |
| Input Dynamic Range | 30-59dB (4 Steps) |
| Bandwidth | 30Hz (Detection) 100Hz (Recording) |
| Classifier | Non-Linear SVM |
| Energy Efficiency | 1.83 μJ/Class. |
| Seizure Detection Accuracy | 95.1% |
| False Alarm | 0.94% |
| Latency | <2 s |

DBE

| Parameter | JSSC 10 [1]<br>MIT<br>N. Verma | JSSC 11<br>MIT<br>J. Kwong | JSSC 11<br>MEC<br>M. Altaf | JSSC 12 [3]<br>MIT-MIT<br>Lee | This Work |
|---|---|---|---|---|---|
| Supply (V) | 1 | 0.7 | 0.4-1.2 | 1.0 | 1.0 |
| On-Chip Classification | X | O | X | O | O |
| DBE Area (mm²) | 2.95<br>(FE only) | 2.73<br>(FE only) | N/A | 8.18<br>(FE+CE, w/o<br>excluding SRAM) | 5.45<br>(FE+CE,<br>excluding RAM) |
| # of Channels | 1 | 1 | 1 | 8 | 8 |
| Classifier Type | (Off-chip)<br>Non-Linear SVM | (Off-chip)<br>/Feature Extraction | - | (On-Chip)<br>Linear SVM | (On-Chip)<br>Non-Linear SVM |
| Seizure Detection Accuracy<br>(Batting/Acc) (%) | N/A | N/A | N/A | 87.0/ 84.4/ 71.2 | 88.6/ 95.6/ 93.2 |
| False Alarm Rate<br>(Batting/Acc) (%) | N/A | N/A | N/A | 2.5/ 4.3/ 14.7 | 0.67/ 0.94/ 1.81 |
| Energy Efficiency | 0.23uJ<br>/Feature Vector | 4.83uJ<br>/Feature Extraction | 47 pJ/cycle* | 1.49uJ/<br>Classification** | 1.31uJ<br>/Classification** |
| DBE Clock Speed | N/A | 10MHz | 1MHz | 5.12MHz (8ch) | 32kHz (8ch) |
| On-Chip Storage | X | X | X | 64KB | 96KB |
| Technology | 0.18μm CMOS | 0.13μm CMOS | 90nm LP | 0.18μm CMOS | 0.18μm CMOS |
| Application | Wearable EEG | Implantable EEG | Wearable EEG | Wearable EEG | Wearable EEG |

* It is unknown how many cycles are needed for one Feature Extraction.
** Total Energy of DBE = Classification + Feature Extraction.

MACHINE-BASED PATIENT-SPECIFIC SEIZURE CLASSIFICATION SYSTEM

PRIORITY

This U.S. Non-Provisional Patent Application claims benefit under 35 U.S.C. 119(e) to U.S. Provisional Patent Application No. 61/765,280 entitled "MACHINE-BASED PATIENT-SPECIFIC SEIZURE CLASSIFICATION SYSTEM" that was filed on Feb. 15, 2013, the contents of the above-identified provisional application being incorporated herein, in entirety, by reference.

TECHNICAL FIELD

The present disclosure relates to electronic medical devices for monitoring and treatment, and more particularly, to a system-on chip (SoC) for detecting and treating a medical condition.

BACKGROUND

At least one stressful and dangerous issue facing epileptic patients is the possible random and sudden occurrence of seizure. One manner in which the impact of seizure may be reduced involves detecting precursors of an oncoming seizure and implementing treatment to suppress it. Partially and/or fully integrated systems have been developed that attempt to detect precursors of seizure onset electrically, as well as clinically, seconds before a seizure occurs, and to combine this detection with neurostimulation in an effort to suppress the seizure. In implementing such integrated detection and treatment systems, minimizing the detection delay (e.g., less than 2 s for real time suppression) while maintaining high detection rate is challenging. Previous attempts were limited by either a long latency or a low detection rate. For example, in one system 100% detection rate has been achievable with a poor latency of 13.5 s, which makes it unsuitable for a real-time application. Another existing system exhibits good latency (e.g., less than 2 s) using a Linear Support Vector Machine (LSVM) classifier, but the detection rate (e.g., 84.4%) was not high enough and the average false alarm rate (e.g., max. 14.7%) was too high for practical use due to an intermittent limit of the LSVM.

BRIEF DESCRIPTION OF THE DRAWINGS

Features and advantages of various embodiments of the claimed subject matter will become apparent as the following Detailed Description proceeds, and upon reference to the Drawings, wherein like numerals designate like parts, and in which:

FIG. 10 illustrates example physical and performance characteristics for a digital back-end (DBE) in accordance with at least one embodiment of the present disclosure;

FIG. 11 illustrates example physical and performance characteristics for an AFE in accordance with at least one embodiment of the present disclosure; and FIG. 12 illustrates an example DBE and AFE performance comparison in accordance with at least one embodiment of the present disclosure.

Although the following Detailed Description will proceed with reference being made to illustrative embodiments, many alternatives, modifications and variations thereof will be apparent to those skilled in the art.

DETAILED DESCRIPTION

This disclosure is directed to a machine-based patient-specific seizure classification system. In general, embodiments of the present disclosure may comprise a system-on-chip (SoC) including a hardware-efficient log-linear engine to realize non-linear support vector machine (NLSVM)-based seizure detection. It is possible for an SoC consistent with the present disclosure to achieve greater than 95% detection accuracy with less than 1% false alarm and less than 2 s latency. An example implementation may further include an embedded 96 kB on-chip SRAM to store raw EEG data upon seizure events for further analysis by physicians.

Figure 1:
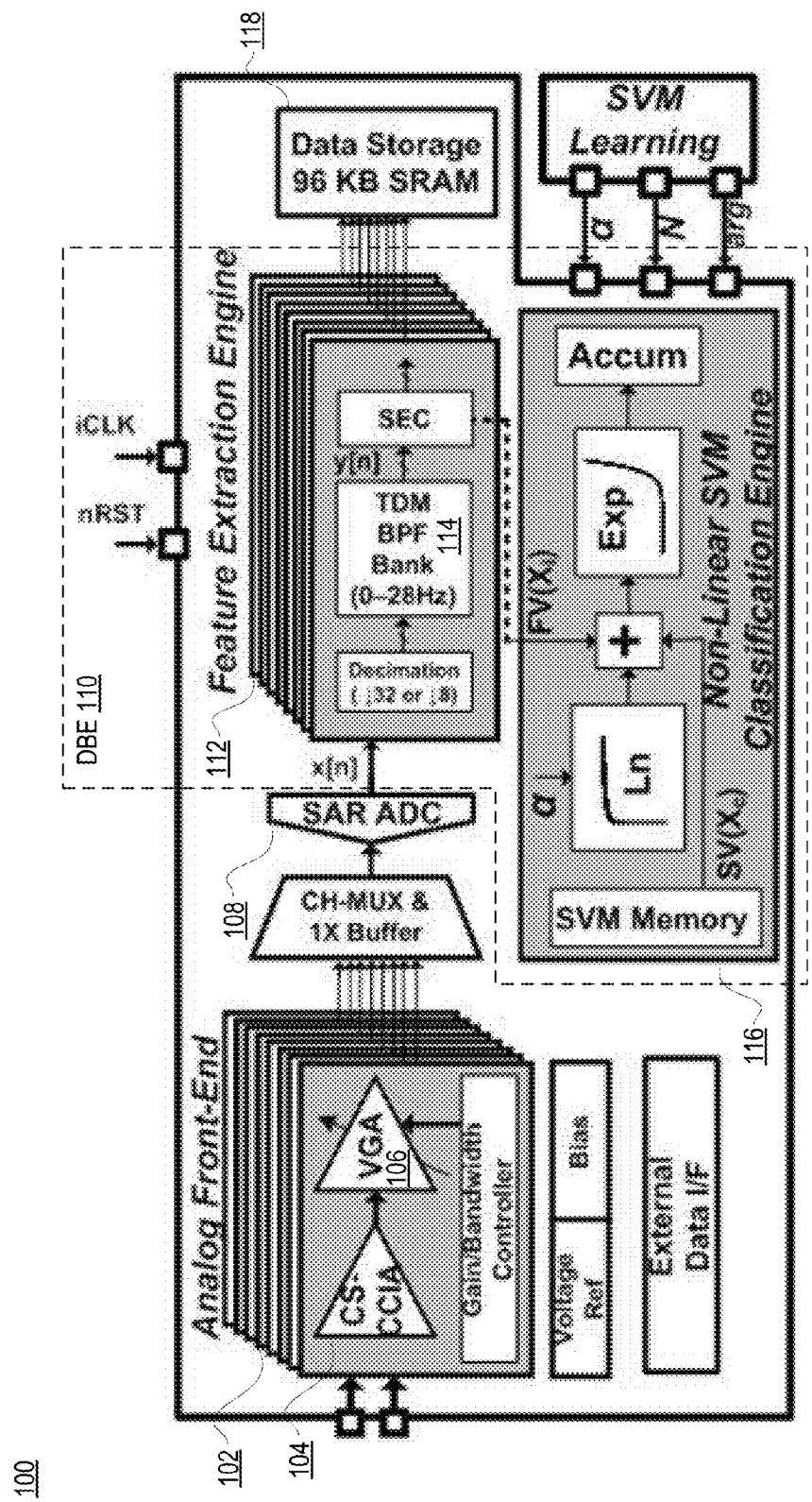
FIG. 1 illustrates an example of an eight-channel scalable electroencephalography (EEG) SoC architecture in accordance with at least one embodiment of the present disclosure.

FIG. 1 illustrates an example of an eight-channel scalable electroencephalography (EEG) SoC architecture in accordance with at least one embodiment of the present disclosure. SoC 100 may comprise analog front end (AFE) 102 including eight-channel chopper-stabilized capacitive-coupled instrumentation amplifier (CS-CCIA) 104, with each channel being followed by variable gain amplifier 106. An analog-to-digital converter (A/D) stage including at least a multiplexer and a 10-bit successive approximation analog-to-digital converter (10-b SAR-A/D) 108 may be to convey signals between AFE 102 and digital back end (DBE) 110. A 10-b SAR-A/D may be employed because the detection rate saturates at over 10 bits. In one embodiment, DBE 110 may perform patient-specific seizure detection processing with multichannel feature extraction (MFE) engine 112 using Time Division Multiplex band-pass filter (TDM-BPF) 114 and NLSVM classification engine 116. SoC 100 may also include embedded SRAM 118 for data storage.

At least one important consideration when integrating multiple channels is minimizing hardware cost while maintaining accuracy. In one example implementation, MFE engine 112 may be based on a seizure detection algorithm using seven filter banks, which may be the most hardware-intensive portion of MFE engine 112, along with real-time processing of eight channels. For example, each of the eight channels may have a 44-tab 7 band-pass filters (BPFs).

Figure 2:
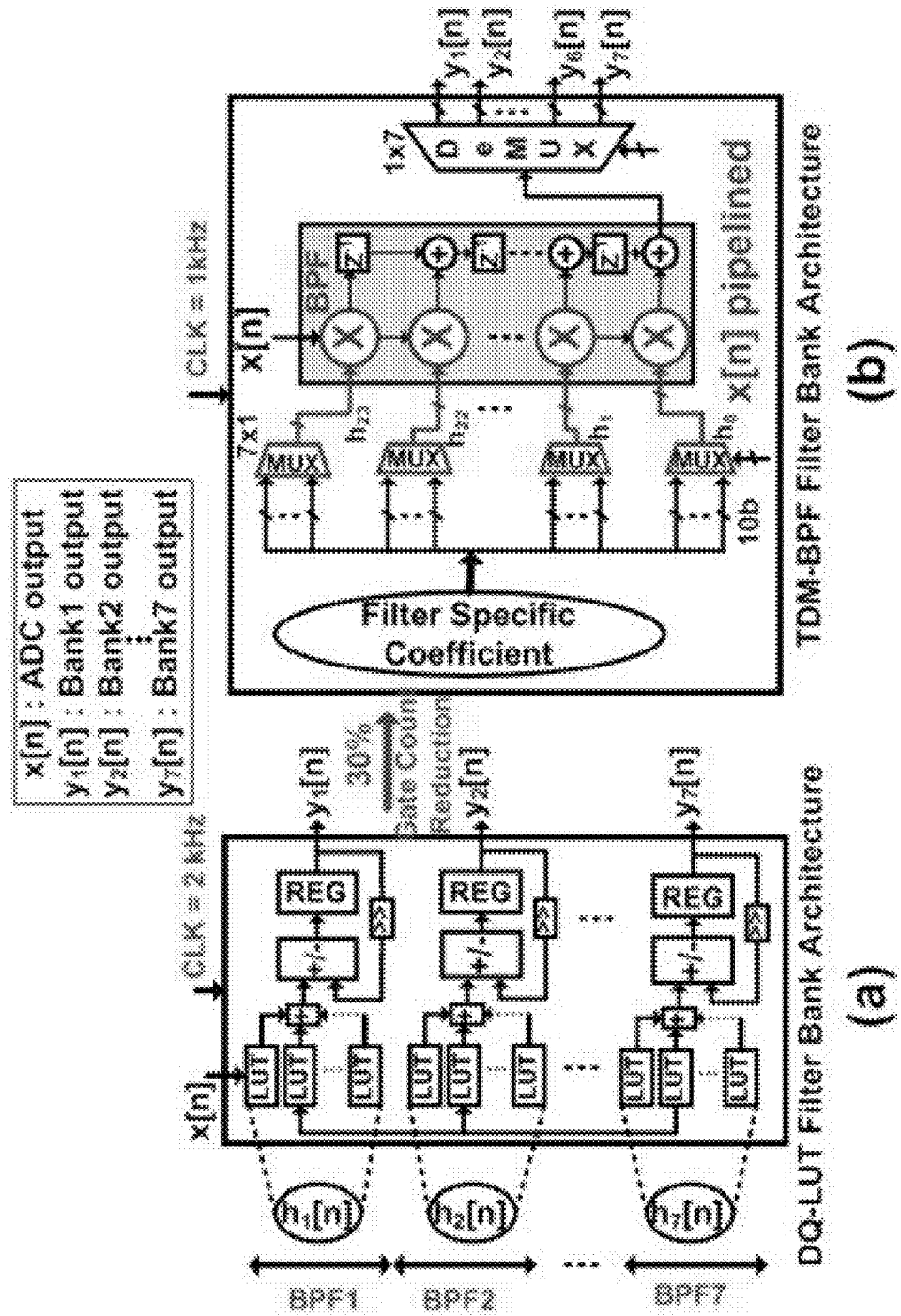
FIG. 2 illustrates an example time division band-pass filter (TDM-BPF) and an example distributed quad look-up table (DQ-LUT) in accordance with at least one embodiment of the present disclosure.

FIG. 2 illustrates an example time division band-pass filter (TDM-BPF) and an example distributed quad look-up table (DQ-LUT) in accordance with at least one embodiment of the present disclosure. As illustrated in diagrams (a)-(b) at 200, DQ-LUT (a) reduces the area of each BPF by replacing multipliers with LUT, but it still uses 8×7=56 BPFs. On the other hand, TDM-BPF (b) uses only one BPF per channel with half the clock while maintaining the same throughput. As all the coefficients in each BPF are fixed values, we can pipeline the inputs by time multiplexing the multipliers among the seven BPFs without any extra overhead of storing the intermediate (tapped) input values. Operating in this manner is possible because only the coefficient settings for each BPF are switching at 8× with the same tapped input being shared (e.g., pipelined) by all the BPF's. This configuration reduces gate counts by 30% as compared to a DQ-LUT configuration, and energy efficiency of 0.43 µJ/Feature Vector (FV) may be achieved.

Figure 3:
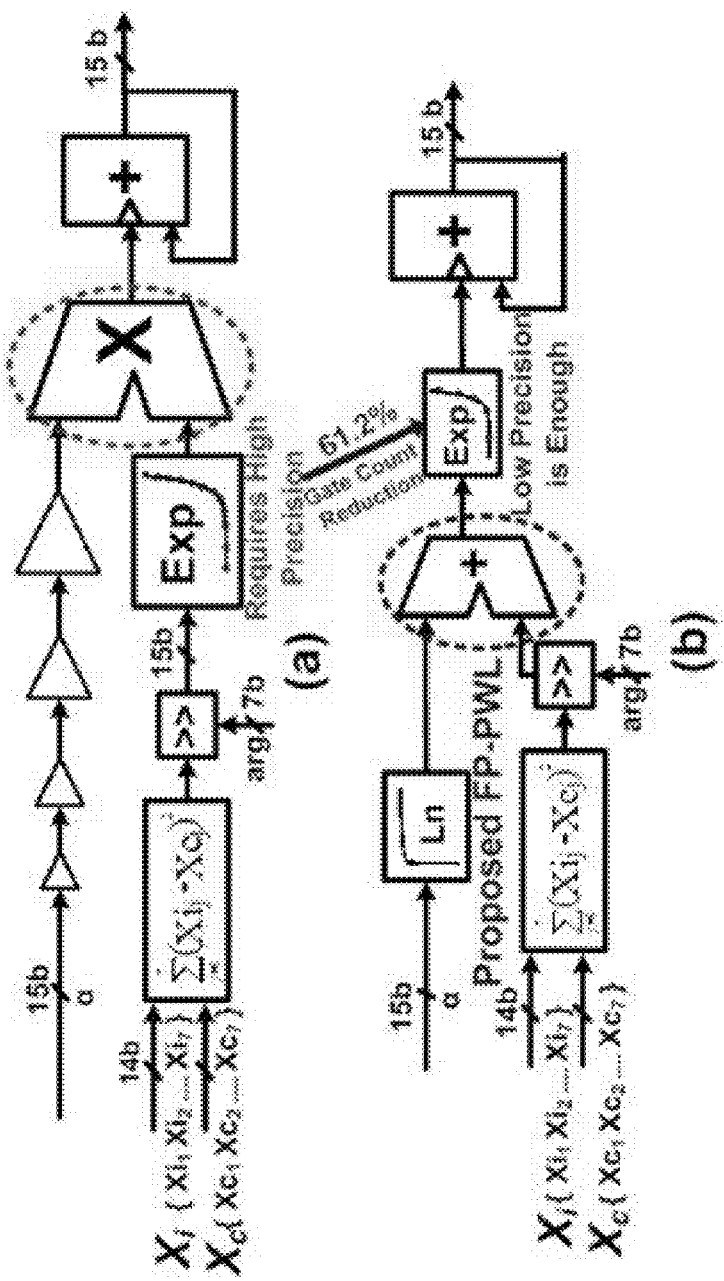
FIG. 3 illustrates an example conventional eye-ball Gaussian basis function (GBF) and an example log-linear GBF (LL-GBF) for non-linear support vector machine (NSLVM) implementation in accordance with at least one embodiment of the present disclosure.

FIG. 3 illustrates an example conventional eye-ball Gaussian basis function (GBF) and an example log-linear GBF (LL-GBF) for NSLVM implementation in accordance with at least one embodiment of the present disclosure. NLSVM with GBF, as illustrated in function (a) at 300, may ensure higher detection rate and lower false alarm rate than a linear support vector machine (LSVM) by the non-linear decision boundary between seizure and non-seizure FV, but at a cost of increased hardware complexity. The log-linear GBF engine (LL-GBF), as illustrated in function (b) at 300, may achieve hardware-efficient NLSVM implementation. Noting that GBF already includes an antilog (e.g., exponential function (Exp)), the LL-GBF linearizes the GBF at just an extra overhead of a natural log (ln) block. This pushes the Exp back to a later stage in function (b), and thus, a lower-precision EF (LPEF) is accurate enough for practical use while realizing a substantial reduction (e.g., 61.2%) in gate count. The LPEF also allows for the use of Floating-Point Piecewise Linear (FP-PWL) segments rather than more hardware-intensive Coordinate Rotation Digital Computer (CORDIC) or Taylor series expansion. Moreover, the 15 b FP multiplier in function (a) may be replaced by a 15 b FP adder in function (b) to further save hardware. As a result, the LL-GBF engine may improve energy efficiency by 15.6% to 0.39 µJ/operation while saving area by 28.2% when compared to the eye-ball GBF.

Figure 4:
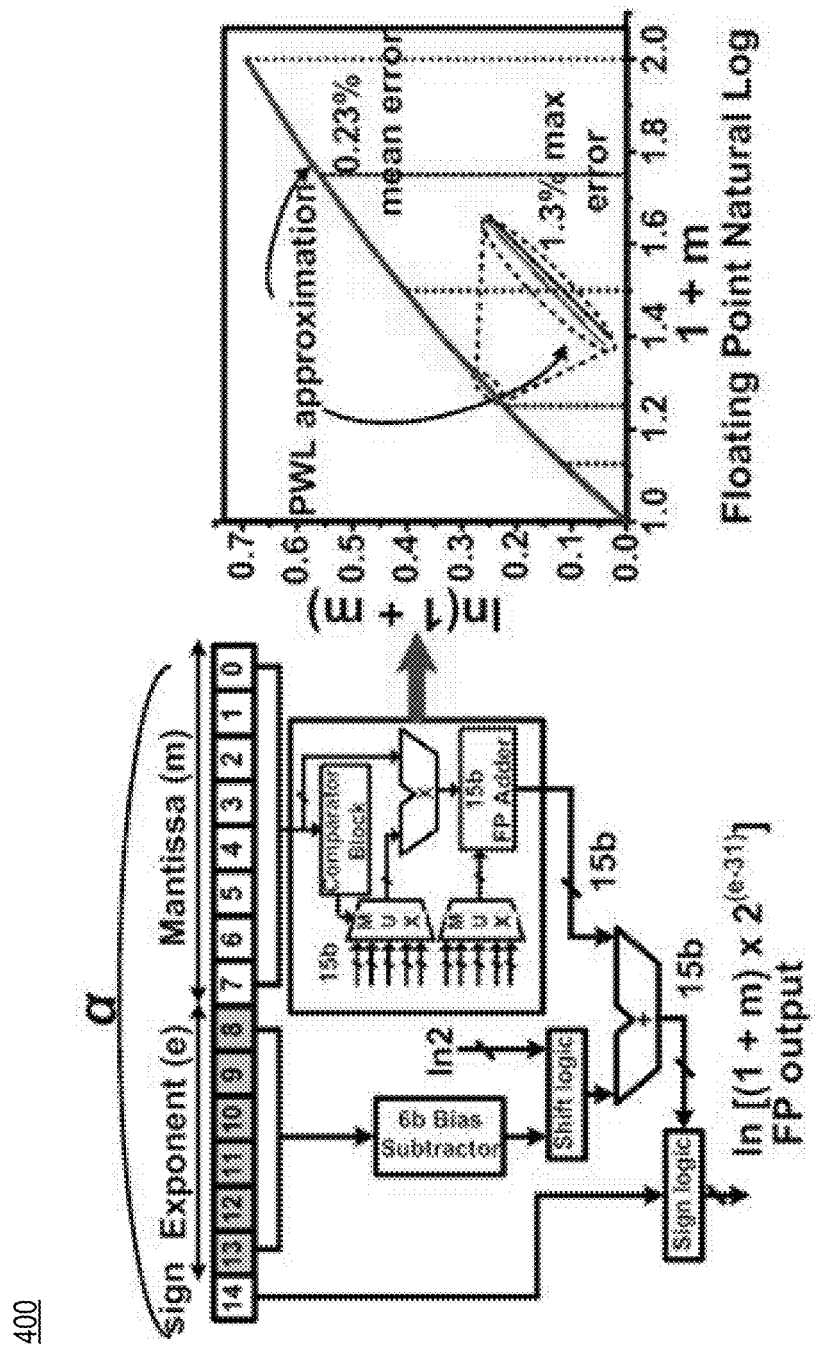
FIG. 4 illustrates example hardware-efficient floating point piecewise linear (FP-PWL) natural log architecture in accordance with at least one embodiment of the present disclosure.

FIG. 4 illustrates example hardware-efficient floating point piecewise linear (FP-PWL) natural log architecture in accordance with at least one embodiment of the present disclosure. As illustrated at 400, the ln of the 15 b floating point input $(1+m)\times 2^{e-31}$ may be computed as $\ln 2\times(e-31)+\ln(1+m)$, where $\ln(1+m)$ is approximated using five linear intervals optimized for high accuracy and efficient hardware implementation. Previous solutions may also utilize five linear intervals for FP single precision PWL, but it is for the base 2 log with maximum error of 5%. The ln of an 8-bit precise mantissa ($0 \le m \le 1$) may be computed using PWL, where the input range of mantissa may be determined by a 5 b one hot encoding comparator block that then feeds the input to specific block for further linear computation. The FP-PWL illustrated at 400 in FIG. 4 may exhibit single cycle latency with 0.23% mean error for the computation of 15 b custom FP ln computation. When combined with a LL-GBF engine such as disclosed in FIG. 3 for seizure detection, the resulting maximum deviation is only 0.5% P in the overall seizure detection rate.

Figure 5:
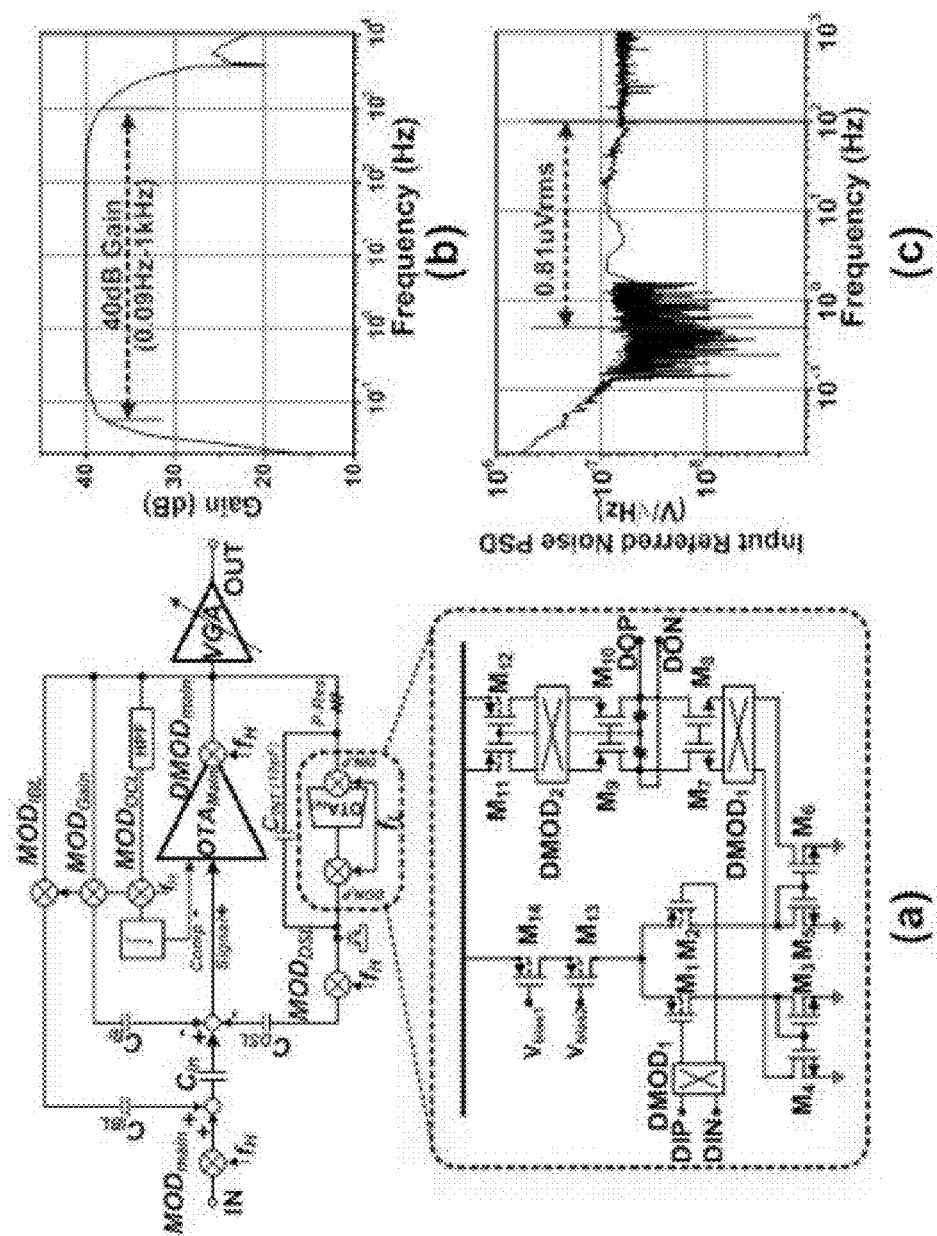
FIG. 5 illustrates an example analog front end (AFE) signal diagram with a direct current servo loop (DSL) chopper structure and a chopper-stabilized capacitive-coupled instrumentation amplifier (CS-CCIA) with measured performance including a gain curve and input-referred noise power spectral density in accordance with at least one embodiment of the present disclosure.

FIG. 5 illustrates an example analog front end (AFE) signal diagram with a direct current servo loop (DSL) chopper structure and a chopper-stabilized capacitive-coupled instrumentation amplifier (CS-CCIA) with measured performance including a gain curve and input-referred noise power spectral density in accordance with at least one embodiment of the present disclosure. In particular, the diagram at 500 shows an example structure of a channel in the eight-channel AFE with a CS-CCIA 104 (e.g., 40 dB) and example corresponding measurement results. CS-CCIA 104 may be compensated with an Offset Cancellation Loop (OCL) to reduce chopping spikes at $f_H$=4 kHz. As a main chopper ($MOD_{main}$) is placed before a DC blocking capacitor, low input impedance may be boosted by a Impedance Boosting Loop (IBL) that provides current partially from the output. In an environment where SoC 100 may be worn on a patient's skin, electrode DC Offset (EDO) may reach up to hundreds of mV, and this may be mitigated by a DC servo loop that achieves AC coupling. However, placing an $OTA_{INT}$ within the DSL's integrator may elevate noise generated by CS-CCIA 104, since all the active components within DSL loop are completely out of the main chopper $MOD_{Main}$, and hence, the noise from the DSL is directly added into the "modulated baseband signal", which cannot be removed by the $DMOD_{Main}$. As a result, the noise level may be elevated by 10.1% when DSL is activated. To solve this problem, another chopper ($MOD_{DSL}$ and $DMOD_{DSL}$ at $f_L$=500 Hz) may be added around the $OTA_{INT}$. For example, 500 Hz may be enough for $f_L$ to deal with the DC component, and setting $f_L$ too high will again elevate the noise caused by the chopping spikes. With the DSL chopper, both 1/f, as illustrated at (b), and channel noise, as illustrated at (c), introduced by $M_1$-$M_{10}$ are effectively modulated and filtered. The CS-CCIA measurement results shown in (a) and (b) confirm that the DSL chopper may reduce the input-referred noise (e.g., from 0.92 $\mu V_{rms}$ to 0.81 $\mu V_{rms}$ (0.5-100 Hz)). As a result, CS-CCIA 104 may consume 1.6 uA at 1.8V power supply, with NEF of 4.0, which is better than that of existing solutions.

Figure 6:
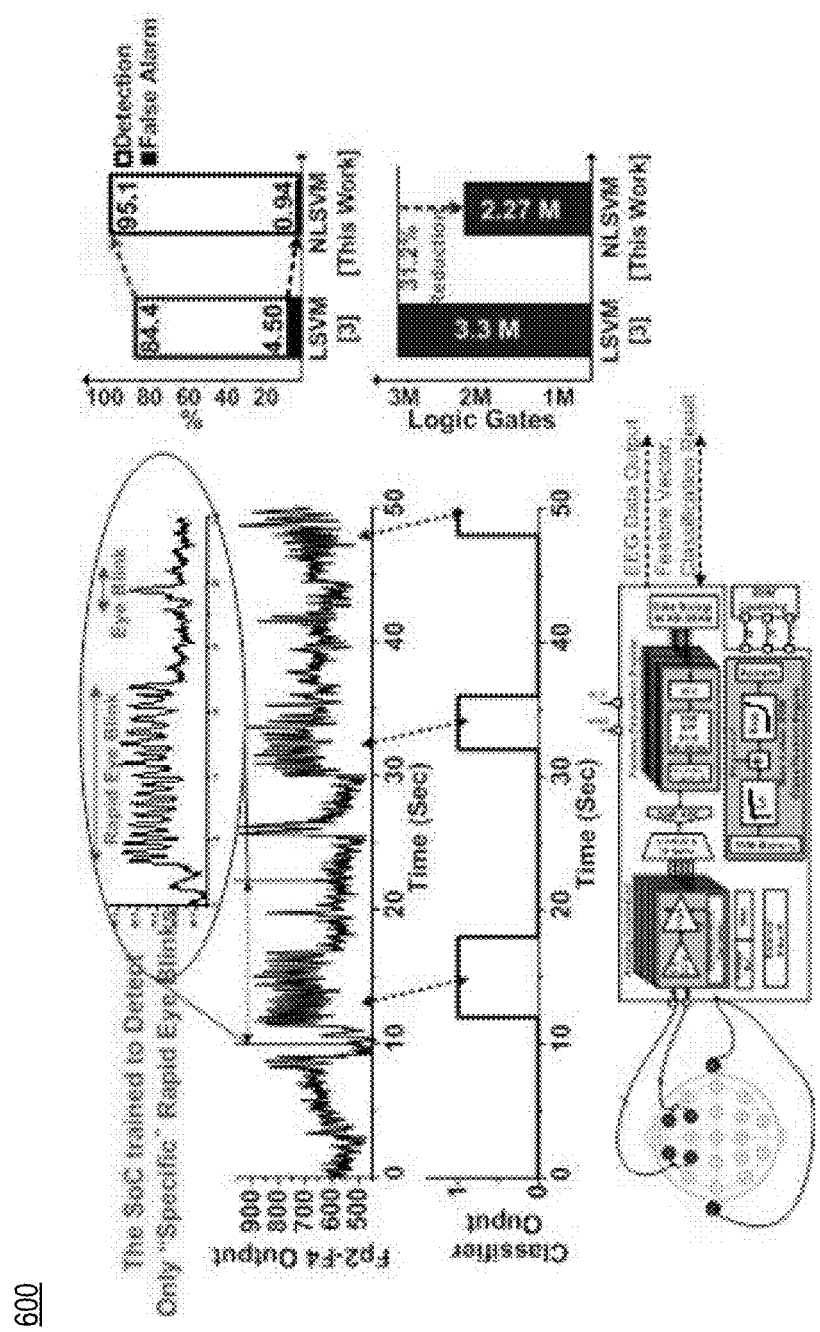
FIG. 6 illustrates example SoC measurements based on a rapid-eye blink classification test in accordance with at least one embodiment of the present disclosure.

FIG. 6 illustrates example SoC measurements based on a rapid-eye blink classification test in accordance with at least one embodiment of the present disclosure. The surface EEG of Fp1-F3 and Fp2-F4 with a common reference are used. In the example of FIG. 6, SoC 100 is trained to detect only a specific rapid eye blinking pattern (10 eye blinks within a 5 s window), and the measurement results verifies that it does not detect other eye blink patterns. On the other hand, in the same test a LSVM-based solution had difficulties in distinguishing the learned pattern from various normal eye blinks. SoC 100 has also been fully tested with MIT-Children's Hospital Boston EEG database, which contains 906 hours of EEG data with 196 seizure events from 23 different epileptic patients. Implementations of SoC 100 have been shown an average detection rate increased to 95.1% and average false alarm dropped to 0.94%, within 2 s latency.

Figure 7:
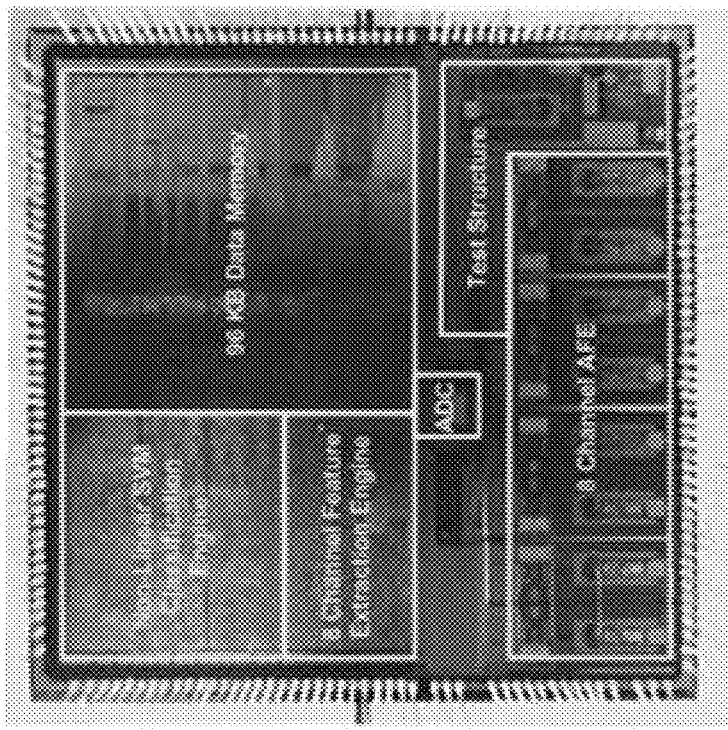
FIG. 7 illustrates an example micrograph and performance summary for an SoC in accordance with at least one embodiment of the present disclosure.

FIG. 7 illustrates an example micrograph and performance summary for an SoC in accordance with at least one embodiment of the present disclosure. Integrated circuit (IC) 700 in FIG. 7 (corresponding to SoC 100 in FIG. 1) fully integrates an 8-channel AFE (corresponding to 102 in FIG. 1), an eight-channel NLSVM-based DBE (corresponding to 110 in FIG. 1), an ADC (corresponding to 108 in FIG. 1), and a 96 kB SRAM (corresponding to 118 in FIG. 1) on 25 mm² 0.18 µm 1P6M CMOS chip. IC 700 has been shown to consume 1.83 µJ/Classification to continuously track patient-specific seizure onset activity. Example physical, operational and/or performance characteristics corresponding to IC 700 are disclosed in table 702.

Figure 8:
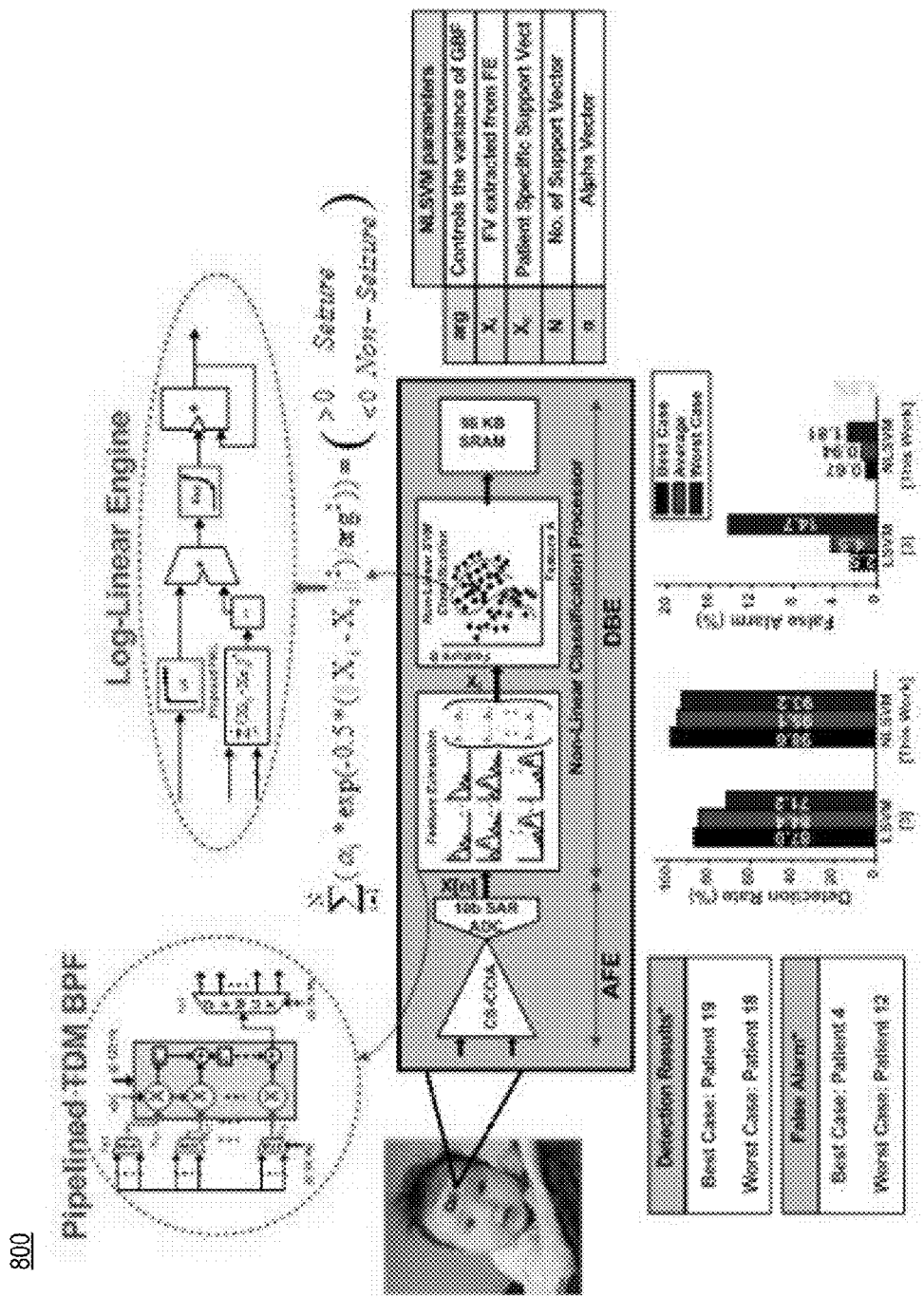
FIG. 8 illustrates an example flow diagram of patient-specific non-linear support vector machine (SVM) classification along with measurement results in accordance with at least one embodiment of the present disclosure.

FIG. 8 illustrates an example flow diagram of patient-specific non-linear support vector machine (SVM) classification along with measurement results in accordance with at least one embodiment of the present disclosure. Each channel data may be passed through FE engine 112 with TDM-BPF 114 to generate Feature Vectors (FVs). Each FV may then be mapped into a seven-dimensional (7-D) feature space, which may then be classified by the non-linear SVM classification boundary by NL-SVM engine 116. The SoC is fully tested with MIT-Children's Hospital Boston EEG database. Compared to previous LSVM-based solutions, embodiments consistent with the present disclosure may improve detection rate from 84.4% to 95.1% average, and may drop false alarm significantly from 4.5% (max 14.7%) to 0.94% (max. 1.81%), all within 2 s latency. Less than 2 second latency for seizure detection is the key for real time seizure suppression system, as in many cases electrical onset of seizures prevail clinical onset by 4-10 s.

Figure 9:
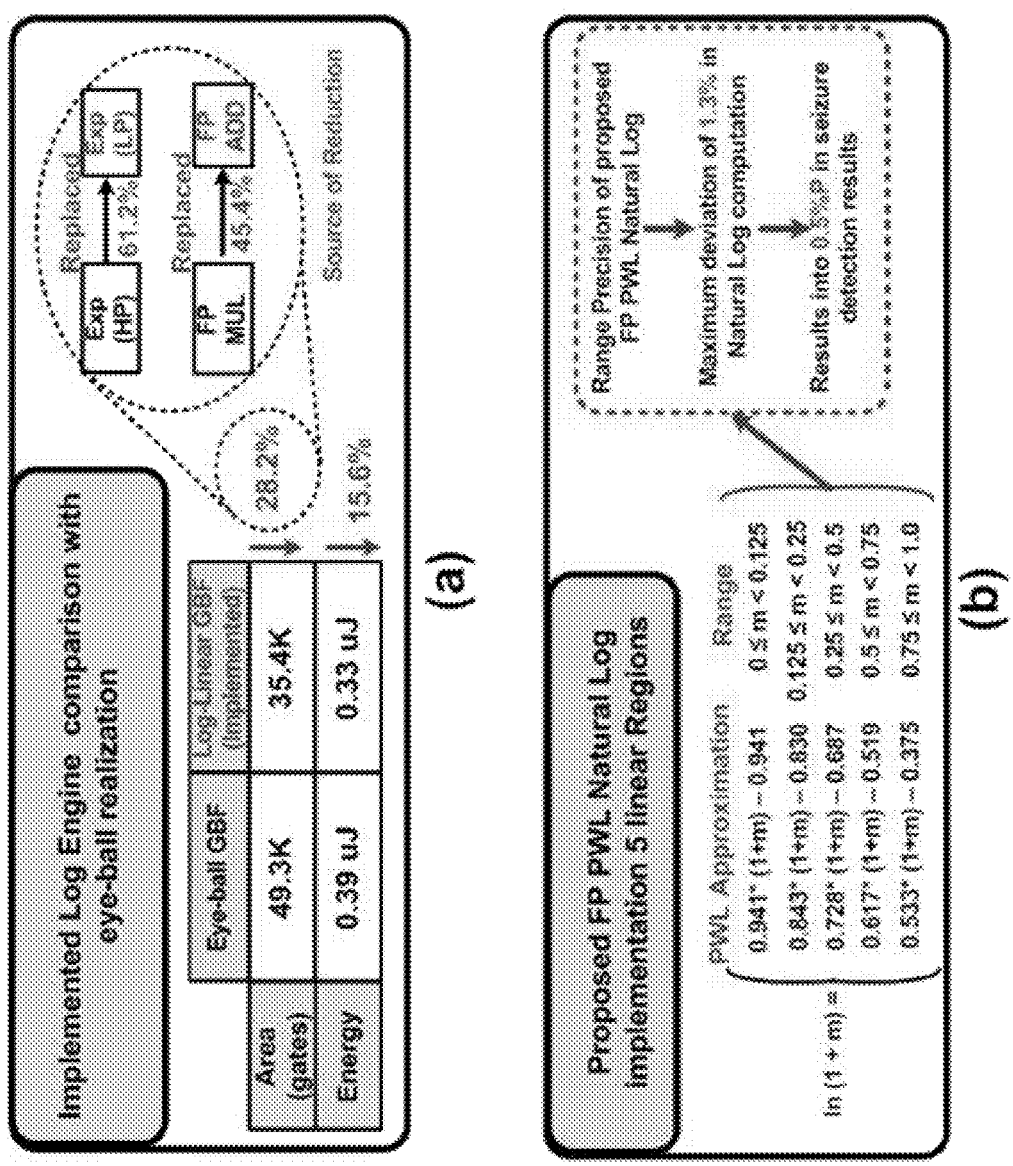
FIG. 9 illustrates example LL-GBF engine advantages over conventional eyeball GBF in area and energy and proposed FP-PWL natural log region breakdowns in accordance with at least one embodiment of the present disclosure.

FIG. 9 illustrates example LL-GBF engine advantages over conventional eyeball GBF in area and energy and proposed FP-PWL natural log region breakdowns in accordance with at least one embodiment of the present disclosure. As previously discussed and summarized at 900 in graph (a), the advantages of LL-GBF over eyeball GBF may include, for example, reduced hardware complexity (e.g., a 28.2% reduction in gate count) and energy consumption. This reduction may be realized through the use of a lower-precision exponential function in LL-GBF, as well as the ability to replace the multiplexer (FP Mult) in the Eye-ball GBF with an adder (FP Add) in the LL-GBF solution. Moreover, graph (b) demonstrates an increase in precision in the LL-GBF solution in that a 1.3% maximum deviation and 0.5% detection precision are possible.

Figure 11:
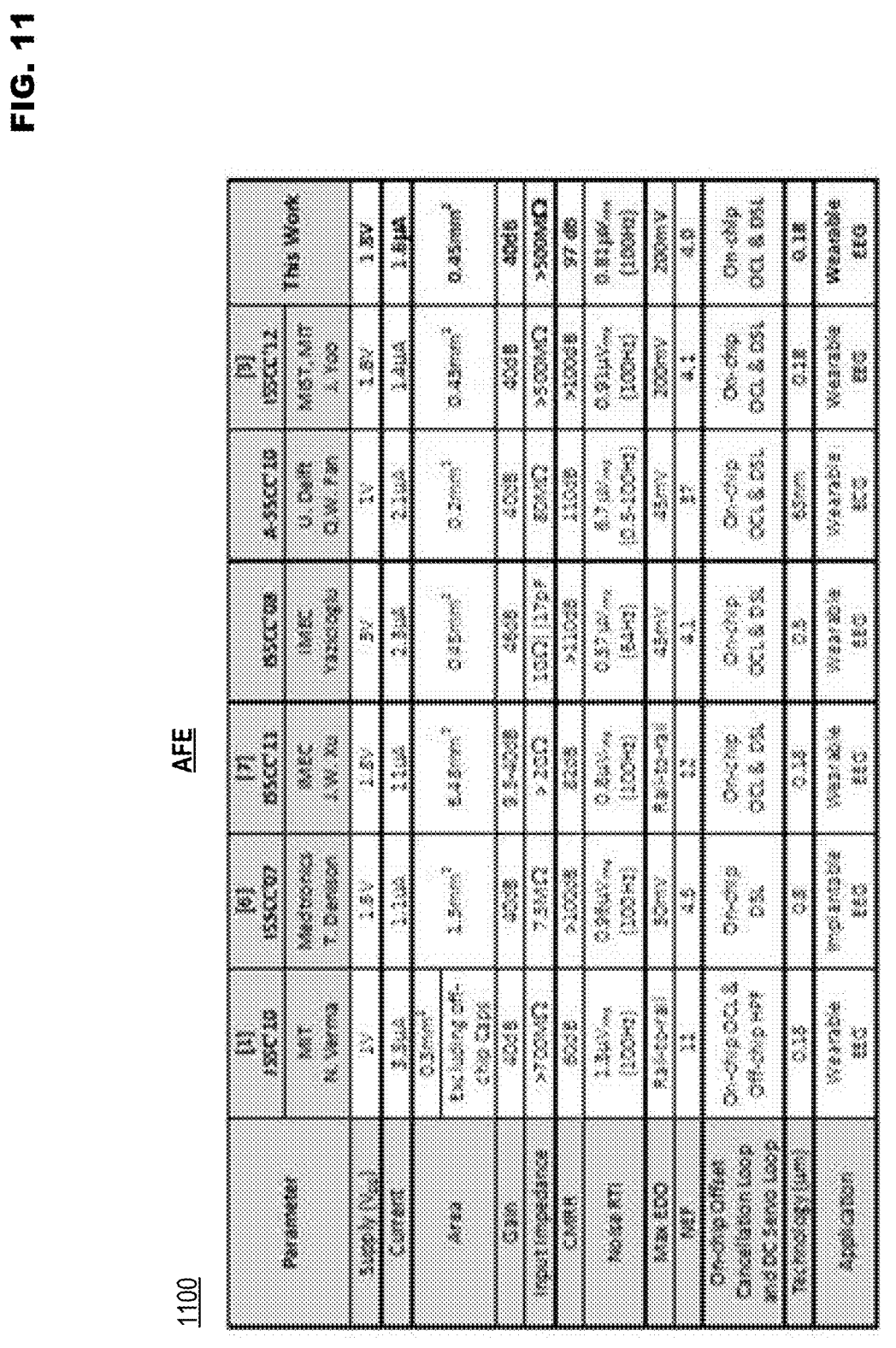
Figure 12:
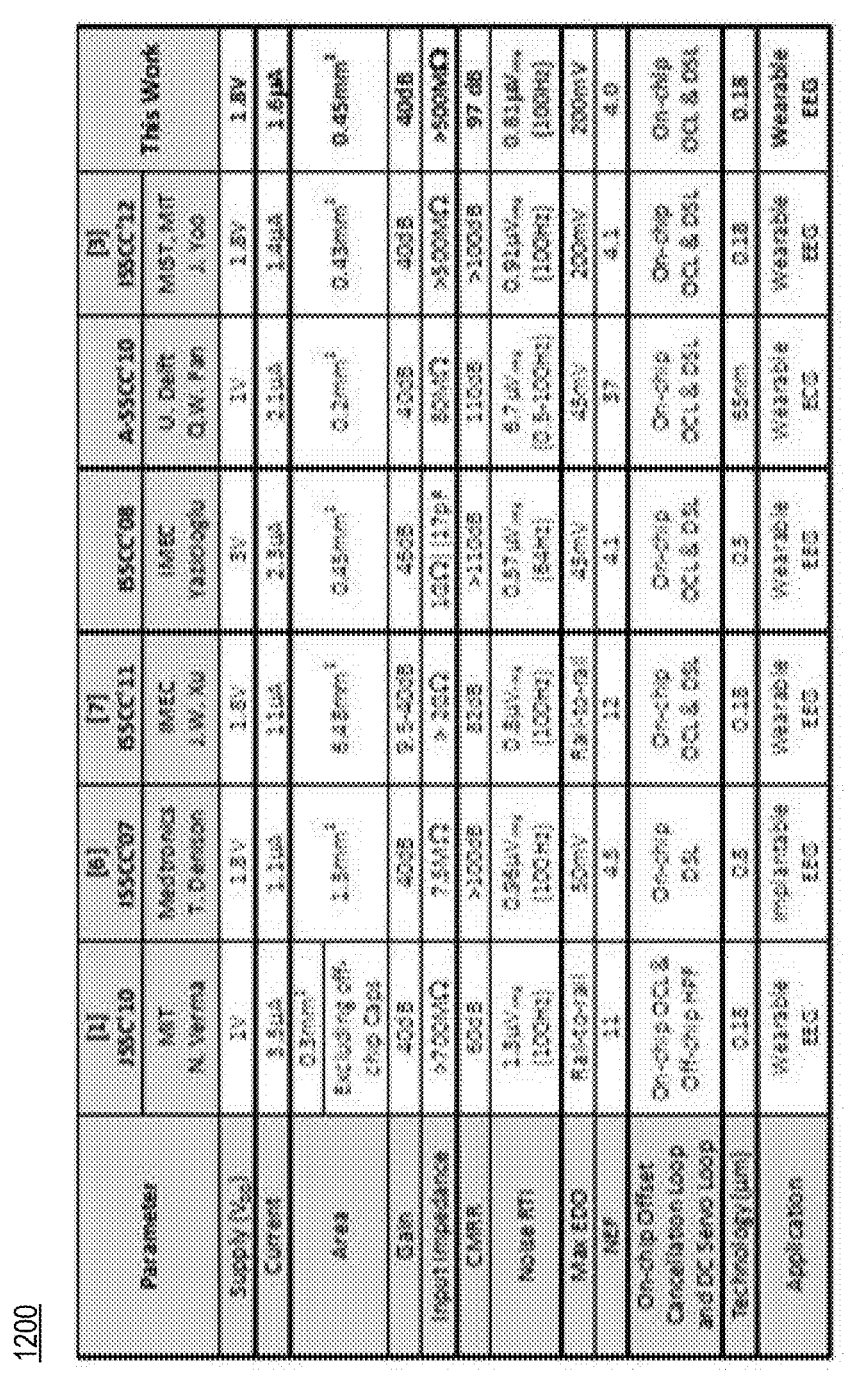

FIG. 10 illustrates example physical and performance characteristics for a digital back-end (DBE) in accordance with at least one embodiment of the present disclosure. In particular, DBE table 1000 in FIG. 10 compares performance information for existing detection and/or treatment systems to performance observed in implementations consistent with embodiments of the present disclosure. FIG. 11 illustrates example physical and performance characteristics for an AFE in accordance with at least one embodiment of the present disclosure. In particular, AFE table 1100 in FIG. 10 compares performance information for existing detection and/or treatment systems to performance observed in implementations consistent with embodiments of the present disclosure. FIG. 12 illustrates an example DBE and AFE performance comparison in accordance with at least one embodiment of the present disclosure. In particular, table 1200 compares the performance characteristics of previous solutions to performance observed in implementations consistent with embodiments of the present disclosure.

While FIG. 8 illustrates various operations according to an embodiment, it is to be understood that not all of the operations depicted in FIG. 6 are necessary for other embodiments. Indeed, it is fully contemplated herein that in other embodiments of the present disclosure, the operations depicted in FIG. 8, and/or other operations described herein, may be combined in a manner not specifically shown in any of the drawings, but still fully consistent with the present disclosure. Thus, claims directed to features and/or operations that are not exactly shown in one drawing are deemed within the scope and content of the present disclosure.

As used in this application and in the claims, a list of items joined by the term "and/or" can mean any combination of the listed items. For example, the phrase "A, B and/or C" can mean A; B; C; A and B; A and C; B and C; or A, B and C. As used in this application and in the claims, a list of items joined by the term "at least one of" can mean any combination of the listed terms. For example, the phrases "at least one of A, B or C" can mean A; B; C; A and B; A and C; B and C; or A, B and C.

As used in any embodiment herein, the term "module" may refer to software, firmware and/or circuitry configured to perform any of the aforementioned operations. Software may be embodied as a software package, code, instructions, instruction sets and/or data recorded on non-transitory computer readable storage mediums. Firmware may be embodied as code, instructions or instruction sets and/or data that are hard-coded (e.g., nonvolatile) in memory devices. "Circuitry", as used in any embodiment herein, may comprise, for example, singly or in any combination, hardwired circuitry, programmable circuitry such as computer processors comprising one or more individual instruction processing cores, state machine circuitry, and/or firmware that stores instructions executed by programmable circuitry. The modules may, collectively or individually, be embodied as circuitry that forms part of a larger system, for example, an integrated circuit (IC), system on-chip (SoC), desktop computers, laptop computers, tablet computers, servers, smart phones, etc.

Any of the operations described herein may be implemented in a system that includes one or more machine-readable storage mediums having stored thereon, individually or in combination, instructions that when executed by one or more processors perform the methods. Here, the processor may include, for example, a server CPU, a mobile device CPU, and/or other programmable circuitry. Also, it is intended that operations described herein may be distributed across a plurality of physical devices, such as processing structures at more than one different physical location. The storage medium may include any type of tangible medium, for example, any type of disk including hard disks, floppy disks, optical disks, compact disk read-only memories (CD-ROMs), compact disk rewritables (CD-RWs), and magneto-optical disks, semiconductor devices such as read-only memories (ROMs), random access memories (RAMs) such as dynamic and static RAMs, erasable programmable read-only memories (EPROMs), electrically erasable programmable read-only memories (EEPROMs), flash memories, Solid State Disks (SSDs), embedded multimedia cards (eM-MCs), secure digital input/output (SDIO) cards, magnetic or optical cards, or any type of media suitable for storing electronic instructions. Other embodiments may be implemented as software modules executed by a programmable control device.

Thus, this disclosure is directed to a machine-based patient-specific seizure classification system. In general, an example system may comprise a non-linear SVM seizure classification system-on-chip (SoC) with multichannel EEG data acquisition and storage for epileptic patients is presented. The SoC may integrate a hardware-efficient log-linear Gaussian Basis Function engine, floating point piecewise linear natural log, and low-noise, high dynamic range readout circuits. In at least one example implementation, the SoC may consume 1.83 µJ/classification while classifying 8 channel results with an average detection rate, average false alarm rate and latency of 95.1%, 0.94% and <2 s, respectively.

The following examples pertain to further embodiments. In one example there is provided a device. The device may include an analog front-end (AFE) to sense electroencephalography (EEG) information, a digital back end (DBE) including at least a feature extraction (FE) engine and a non-linear support vector machine (NL-SVM) classification engine to determine onset of a seizure based on the EEG information, and an analog-to-digital converter (A/D) stage to convert analog signals provided by the AFE for use by the DFE.

The above example device may be further configured, wherein the device is composed entirely on an integrated circuit (IC) in a system-on-chip (SoC) configuration. In this configuration the example device may be further configured, wherein the SoC further comprises electrodes to sense the EEG information and during operation the SoC may be worn by a patient with the electrodes coupled directly to the patient's skin.

The above example device may be further configured, alone or in combination with the above further configurations, wherein the analog front end comprises a plurality of channels, each of the plurality of channels comprising at least a chopper-stabilized capacitive-coupled instrumentation amplifier (CS-CCIA) and a variable gain amplifier. In this configuration the example device may be further configured, wherein the A/D stage comprises a multiplexer to receive analog signals from the plurality of channels and an A/D to convert the received analog signals into digital signals. In this configuration the example device may be further configured, wherein the A/D is a 10-bit successive approximation A/D (10-b SAR-A/D).

The above example device may be further configured, alone or in combination with the above further configurations, wherein the FE engine comprises a plurality of channels, each of the plurality of channels including a time division multiplex band-pass filter (TDM-BPF) to extract feature vectors (FVs) from the EEG information for use in determining the onset of a seizure.

The above example device may be further configured, alone or in combination with the above further configurations, wherein the NL-SVM classification engine utilizes a log-linear Gaussian basis function (LL-GBF) to determine the onset of a seizure.

The above example device may be further configured, alone or in combination with the above further configurations, wherein the device further comprises a static random access memory to store the EEG information.

In another example there is provided a method. The method may include receiving analog electroencephalography (EEG) information in a device, converting the analog EEG information into digital EEG information, extracting feature vectors (FVs) from the digital EEG information, and determining onset of a seizure based on the extracted FVs.

The above example method may be further configured, wherein the analog EEG information is received via an analog front-end (AFE) comprising a plurality of channels, each of the plurality of channels including at least a chopper-stabilized capacitive-coupled instrumentation amplifier (CS-CCIA) and a variable gain amplifier. In this configuration the example method may be further configured, wherein the analog EEG information is converted into digital EEG information via an analog-to-digital converter (A/D) stage comprising a multiplexer to receive analog signals from the plurality of channels and an A/D to convert the received analog signals into digital signals. In this configuration the example method may be further configured, wherein the A/D is a 10-bit successive approximation A/D (10-b SAR-A/D).

The above example method may be further configured, alone or in combination with the above further configurations, wherein the FVs are generated by a feature extraction (FE) engine comprising a plurality of channels, each of the plurality of channels comprising a time division multiplex band-pass filter (TDM-BPF) to extract the FVs. In this configuration the example method may be further configured, wherein determining the onset of a seizure based on the FVs comprises mapping the FVs into a seven-dimensional (7-D) feature space and classifying the FVs using a non-linear support vector machine (NL-SVM) classification engine.

The above example method may further comprise, alone or in combination with the above further configurations, if the onset of a seizure is determined, causing electrical stimulation to commence to prevent occurrence of the seizure.

In another example there is provided a device having means to carry out any of the above example methods.

In another example there is provided at least one machine-readable storage medium having stored thereon, individually or in combination, instructions that when executed by one or more processors result in the following operations comprising receiving analog electroencephalography (EEG) information, converting the analog EEG information into digital EEG information, extracting feature vectors (FVs) from the digital EEG information, and determining on the onset of a seizure based on the extracted FVs.

The above example medium may be further configured, wherein the analog EEG information is received via an analog front-end (AFE) comprising a plurality of channels, each of the plurality of channels including at least a chopper-stabilized capacitive-coupled instrumentation amplifier (CS-CCIA) and a variable gain amplifier. In this configuration the example medium may be further configured, wherein the analog EEG information is converted into digital EEG information via an analog-to-digital converter (A/D) stage comprising a multiplexer to receive analog signals from the plurality of channels and an A/D to convert the received analog signals into digital signals. In this configuration the example medium may be further configured, wherein the A/D is a 10-bit successive approximation A/D (10-b SAR-A/D).

The above example medium may be further configured, alone or in combination with the above further configurations, wherein the FVs are generated by a feature extraction (FE) engine comprising a plurality of channels, each of the plurality of channels comprising a time division multiplex band-pass filter (TDM-BPF) to extract the FVs. In this configuration the example medium may be further configured, wherein determining on the onset of a seizure based on the FVs comprises mapping the FVs into a seven-dimensional (7-D) feature space and classifying the FVs using a non-linear support vector machine (NL-SVM) classification engine.

The above example medium may further comprise, alone or in combination with the above further configurations, instructions that when executed by one or more processors result in the following operations comprising if the onset of a seizure is determined, causing electrical stimulation to commence to prevent occurrence of the seizure.

The terms and expressions which have been employed herein are used as terms of description and not of limitation, and there is no intention, in the use of such terms and expressions, of excluding any equivalents of the features shown and described (or portions thereof), and it is recognized that various modifications are possible within the scope of the claims. Accordingly, the claims are intended to cover all such equivalents.

What is claimed:

1. A device, comprising:
   an analog front-end (AFE) to generate at least one analog signal representative of electroencephalography (EEG) information;
   a digital back end (DBE) including a feature extraction (FE) engine and a non-linear support vector machine (NL-SVM) classification engine comprising circuitry configured to perform an antilog function on a summation of a first input and a log conversion of a second input to determine onset of a seizure based on at least one digital signal corresponding to the at least one analog signal; and
   an analog-to-digital converter (A/D) stage to convert the at least one analog signal provided by the AFE to the at least one digital signal for use by the DBE.

2. The device of claim 1, wherein the device is composed entirely on an integrated circuit (IC) in a system-on-chip (SoC) configuration.

3. The device of claim 2, wherein the SoC further comprises electrodes to sense the EEG information, wherein the SoC is configured to be worn by a patient with the electrodes coupled directly to the patient's skin.

4. The device of claim 1, wherein the analog front end comprises a plurality of channels, each of the plurality of channels comprising at least a chopper-stabilized capacitive-coupled instrumentation amplifier (CS-CCIA) and a variable gain amplifier.

5. The device of claim 4, wherein the A/D stage comprises a multiplexer to receive analog signals from the plurality of channels and an A/D to convert the received analog signals into digital signals.

6. The device of claim 5, wherein the A/D is a 10-bit successive approximation A/D (10-b SAR-A/D).

7. The device of claim 1, wherein the FE engine comprises a plurality of channels, each of the plurality of channels including a time division multiplex band-pass filter (TDM-BPF) to extract feature vectors (FVs) from the EEG information for use in determining the onset of a seizure.

8. The device of claim 1, wherein the device further comprises a static random access memory to store the EEG information.

9. The device of claim 1, wherein the circuitry configured to perform the log conversion comprises circuitry to linearize the log function into multiple linear segments to approximate the log function.

10. A method, comprising:
    receiving at least one analog signal representative of encephalography (EEG) information;
    converting the at least one analog signal to at least one digital signal;
    extracting feature vectors (FVs) from the at least one digital signal; and
    determining onset of a seizure based on the extracted FVs using a linear support vector machine (NL-SVM) classification engine configured to perform an antilog function on a summation of a first input and a log conversion of a second input; and
    if the onset of a seizure is determined, causing electrical stimulation to commence to prevent occurrence of the seizure.

11. The method of claim 10, wherein the analog signal comprises a plurality of electroencephalography (EEG) information signals received via an analog front-end (AFE) comprising a plurality of channels, each of the plurality of channels including at least a chopper-stabilized capacitive-coupled instrumentation amplifier (CS-CCIA) and a variable gain amplifier.

12. The method of claim 11, wherein the analog signals are converted into digital signals via an analog-to-digital converter (A/D) stage comprising a multiplexer to receive the plurality of analog signals from the plurality of channels and an A/D to convert the received analog signals into digital signals.

13. The method of claim 12, wherein the A/D is a 10-bit successive approximation A/D (10-b SAR-A/D).

14. The method of claim 10, wherein the FVs are generated by a feature extraction (FE) engine comprising a plurality of channels, each of the plurality of channels comprising a time division multiplex band-pass filter (TDM-BPF) to extract the FVs.

15. The method of claim 14, wherein determining the onset of a seizure based on the FVs comprises mapping the FVs into a seven-dimensional (7-D) feature space and classifying the FVs using said non-linear support vector machine (NL-SVM) classification engine.

16. The method of claim 10, wherein the circuitry configured to perform the log conversion comprises circuitry to linearize the log function into multiple linear segments to approximate the log function.

17. One or more non-transitory computer-readable memories having stored thereon, individually or in combination, instructions that when executed by one or more processors result in the following operations comprising:
    receiving at least one digital signal corresponding to at least one analog signal representative of a patient's electroencephalography (EEG) information;
    extracting feature vectors (FVs) from the digital signal;
    determining the onset of a seizure based on the extracted FVs using a non-linear support vector machine (NL-SVM) classification configured to perform an antilog function on a summation of a first input and a log conversion of a second input; and
    if the onset of a seizure is determined, causing electrical stimulation to commence to prevent occurrence of the seizure.

18. The one or more non-transitory computer-readable memories of claim 17, wherein determining on the onset of a seizure based on the FVs comprises mapping the FVs into a seven-dimensional (7-D) feature space and classifying the FVs using said non-linear support vector machine (NL-SVM) classification engine.

19. The one or more non-transitory computer-readable memories of claim 17, wherein performing the log conversion comprises linearizing the log function into multiple linear segments to approximate the log function.

* * * * *